United States Patent [19]

Glucksman

[11] Patent Number: 6,006,136
[45] Date of Patent: *Dec. 21, 1999

[54] HEATING PAD

[75] Inventor: Dov Glucksman, Wenham, Mass.

[73] Assignee: Appliance Development Corp., Wenham, Mass.

[*] Notice: This patent is subject to a terminal disclaimer.

[21] Appl. No.: 08/972,368

[22] Filed: Nov. 18, 1997

Related U.S. Application Data

[63] Continuation of application No. 08/738,891, Oct. 28, 1996, Pat. No. 5,720,774.

[51] Int. Cl.$^6$ .......................................................... A61F 7/00
[52] U.S. Cl. .............................. 607/98; 607/96; 607/114; 165/46; 126/204
[58] Field of Search ........................ 607/96, 104, 98–99, 607/108–112, 114, 152; 165/46; 126/204; 219/212

[56] References Cited

U.S. PATENT DOCUMENTS

5,720,774  2/1998  Glucksman .............................. 607/96

*Primary Examiner*—Cary O'Connor
*Assistant Examiner*—Ryan Carter
*Attorney, Agent, or Firm*—Sofer & Haroun, LLP

[57] ABSTRACT

An electric heating pad is provided, the heating pad having a conductive sheet, the conductive sheet provided with an elongated opening and a perimeter. The conductive sheet is comprised of a flexible and pliable material so that the conductive sheet is capable of following and adhering to the contour of the surface of the human body when applied thereto. A first sheet material, having a seal area disposed on the first sheet material and a perimeter larger than the perimeter of the conductive sheet so as to extend over the conductive sheet to define a sealing edge is provided. A second sheet material, having a seal area disposed on the second sheet material and a perimeter larger than the perimeter of the conductive sheet so as to also extend over the conductive sheet to define a sealing edge is also provided. In this way, when the conductive sheet is placed between the first and second sheet material and when the sealing edges of the first and second sheet material are aligned together, the sealing area and the sealing edges of the first sheet are adhered together with the sealing area and the sealing edges of the second sheet so that the conductive sheet is sealed within the first and second sheet material to define a watertight pouch.

10 Claims, 12 Drawing Sheets

HEATING PAD

CROSS-REFERENCE TO RELATED APPLICATIONS

This application is a continuation of Ser. No. 08/738,891, filed Oct. 28, 1996, which issued Feb. 24, 1998 as U.S. Pat. No. 5,720,774.

FIELD OF THE INVENTION

The present invention relates generally to an electric heating pad wherein a carbon impregnated, non-woven electrically conductive sheet is energized by electric current so that current flow through the electrically conductive sheet generates heat which is used by people or animals to heat certain parts of their body for healing or soothing purposes.

BACKGROUND OF THE INVENTION

Electric heating pads have been used for a long time for healing or soothing bruised areas of the body. Electric heating pads are generally characterized by the fact that they are flexible and therefore can be adapted to parts of the body that need to be heated. The traditional heating pad consists of a rope heater, namely, a heating element where a very fine electric conductor wire is wound around a core which is typically made of glass fibers, and which is manufactured in long-length and cut to the required length and then stitched in a meandering manner onto a substrate made of felt or similar material which supports it in its position. The substructure is subsequently covered by a couple of sheets of vinyl, one on each side of the felt and the vinyl sheets are then adhered together at their peripheral edges to provide a water tight enclosure.

Rope heaters have evolved over the years to where now-a-days, the rope heater is a structure that consists of the aforementioned fiberglass core, surrounded by fine resistance wire. However, the entire heater is subsequently covered by an insulating layer of PVC to prevent contact with the electrically live wire. The rope heater, in its early form or in its present form, is of a diameter that approaches one eighth ("⅛") of an inch and is stitched in a meandering pattern to the supporting felt pad. However, it can be felt from the outside as ridges that are uncomfortable for the user and due to the fact that they are spaced apart between one (1) and one and a half (1½) inches. The typical heating pad therefore will exhibit hot areas where the rope heater is located, and cool areas in between two adjacent heater turns. By contrast, the heating pad of the present invention, incorporating the electrically conductive sheet, would offer an almost continuous and uninterrupted source of heat over the entire surface of the pad alleviating the problem of the non-uniform heat generation as well as the problem of the ripples, caused by the rope heater in the old designs.

Attempts have been made in the past to use an impregnated board as a flexible heater, as U.S. Pat. No. 3,657,516 to Fujihara teaches the use of an impregnated pad as a flexible source of heat. Also, U.S. Pat. No. 4,697,066 to Glucksman, teaches a flexible heater in conjunction with a curling iron as do U.S. Pat. No. 3,099,540 to Eisler, U.S. Pat. No. 3,266,055 to Balder et al., and U.S. Pat. No. 4,485,297 to Grise et al. The latter four patents reference a printed or a diecut heater in contrast with the impregnated carbon electrically conductive sheet as in the present invention. Of interest will also be U.S. Pat. No. 4,710,612 to Lin et al., as well as U.S. Pat. No. 2,473,183 to Watson. One may also mention U.S. Pat. No. 4,791,276 to Midgley et al. which teaches a somewhat different application of a heater in an elongated device meant for thawing pipes in the winter and preventing freezing of gutters, driveways, etc.

The heating pad, according to the present invention, differs from all of the above references insofar as the electrically conductive impregnated sheet is perforated in predetermined locations and that the outer envelope, made of two PVC sheets which are adhered to each other through those perforations. By doing this, one is able to anchor the electrically conductive impregnated sheet in place so as to avoid it from folding over on itself or its shifting within the envelope, which is a problem that would normally be encountered with such large sheets, resulting in over-heating as well as electrically "shorting" of the electrically conductive sheet on to itself. A further advantage associated with the perforation of the pad is that, by running elongated slots along the conductive path of the pad, one is able to isolate certain resistive portions from the main heater and use these resistive portions in order to control the temperature of the heating pad as will be discussed later on.

OBJECTIVES AND SUMMARY OF THE INVENTION

It is an objective of the invention to provide a heating pad that incorporates an electrically conductive sheet which is connected to electrical terminals on either end where current flows through the electrically conductive sheet and generates heat. The electrically conductive sheet being thin, flexible and pliable.

It is a further objective of the invention to provide perforations, in said electrically conductive sheet, which allow the adhering of the outside, protective PVC sheets to each other and thereby retain the electrically conductive sheet in its place to prevent the shifting or the overlapping of parts of the electrically conductive sheet thereby avoiding overheating or shorting of the sheet onto itself.

It is a further objective of the invention to provide for elongated perforations in the direction of the current flow in the electrically conductive sheet which create separate resistors which can be used to control the temperature of the pad at different temperature settings.

It is yet a further objective to provide more than one (1) circuit within the heating pad so that different areas of the heater may operate at different temperatures from other parts of the heater.

It is yet another objective of the invention to sandwich the electrically conductive sheet between two (2) layers of flexible foamed plastic so as to add substance to the otherwise very thin pad and also to allow for the attenuation of temperature fluctuations of the pad caused by the turning on and off of the current by the thermostat; as the mass of the foam and the air that is trapped in it, will retain some heat while the electrically conductive sheet with its minimal mass would cool off very rapidly.

It is another objective of the invention to provide the pad with thermostats which are set to control the temperature of the pad so that the user would have a comfortable surface temperature.

It is yet another objective of the invention to provide a heating pad with external controlling means that will cause the heating pad to operate at more than one temperature.

A final objective of the invention is to use circuit means to vary the power input to the heating pad so that the temperature of the heating pad would be controlled by the amount of electric power supplied to the pad.

In accordance with the present invention, the heating pad consists of an electrically conductive sheet which is a non-woven pad known by the Trade Mark NOMEX manufactured by the E. I. DuPont Co. of Wilmington Del., U.S.A. The pad consists of fibers of polyester held together with a binder to form a permeable sheet which subsequently is soaked in a bath of suspended carbon black powder which tends to adhere to the non-woven fibers so that when it is finally dehydrated, it forms a continuous medium with a predetermined electric conductivity. The conductivity or resistivity, of the impregnating sheet is a function of the length of time that the non-woven sheet is kept in the solution of carbon. The longer the time, the greater the deposit of carbon and consequently, the greater the electrical conductivity. The shorter the time, the less carbon is absorbed into the non-woven sheet and the lower the conductivity or the higher the resistivity. It is therefore important that the non-woven substrate be kept in the carbon solution for a controllable and well-maintained period of time.

By applying a strip of electrically conductive tape to the two ends of the carbon impregnated sheet, electric current will flow through the sheet in parallel flow lines from one electrically conductive tape to the other and as a result, heat will be generated uniformly throughout the sheet and be transmitted outwardly to the environment. Heat, being generated is proportional to the current that flows through the sheet, it will therefore be inversely proportional to the resistance, i.e. the higher the resistance the lower the current and the lower the heat being generated.

Since the sheet, with it's two conductive tape strips, is basically at line voltage of 120V, it needs to be shielded from contact by persons using the heating pad. Therefore, the electrically conductive sheet is covered by two pads of plastic foam, one on each side of the electrically conductive sheet, the foam serving a dual purpose: to provide electrical insulation and to act as a temperature attenuator, so that the temperature fluctuations of the pad, which is being turned on and off by the controlling thermostat, would be absorbed by the mass of the foam and the air trapped inside the foam. This would diminish the fluctuation of the temperature that is sensed on the surface of the pad itself.

In order to hold the foam in place and to provide for added electrical insulation, the foam sheets are themselves covered by two outer layers of poly vinyl chloride (PVC) which are being adhered onto each other through perforations that extend through the foam and through the electrically conductive sheet. The outer vinyl covers are also sealed along their entire periphery and also sealed onto the electric cord, which is also insulated by a PVC insulation so as to prevent the possibility of any moisture entering into the heating pad structure.

In order to control the temperature of the heating pad so that the desired comfort level and therapeutic benefits are achieved, each heating pad is provided with at least one thermostat. The thermostat is set at a predetermined temperature, and when the electrically conductive sheet reaches that temperature, the thermostat will open the electrical circuit which will not be closed until the temperature has fallen below a predetermined temperature at which the thermostat will close again, and allow for current to flow through the electrically conductive sheet. Since more than one temperature setting would be required by the users of the heating pad; as certain users would like a hotter heating pad and certain users would like a cooler heating pad, a system for temperature control has been devised for the heating pad according to this invention. To achieve more than one temperature setting a certain portion of the heating pad was isolated from the remainder of the heating pad by means of two elongated cuts that run along the direction of the current flow in the electrically conductive sheet (perpendicular to the strips of conductive tap). At a certain location in the above mentioned strip, a secondary electrical contact is positioned. When this second contact, which consists of an electrically conductive strip and a electric lead, is short to one side or the other side of the of the electrically conductive sheet, the current will then flow between that particular contact point and the side of the opposite polarity. Since the distance between the second contact and the other polarity is smaller than the distance that exists between the two conductive strips on the edges of the electrically conductive sheet, the resistance between the second contact and the strip of the opposite polarity would be much lower, proportionately to the distance, and therefore a greater amount of current would flow in the isolated area. If we place a thermostat in that isolated area, that thermostat would sense a higher temperature than would be sensed by the rest of the heating element and consequently it would shut the power to the heater sooner than had it been placed in the main heating element area thereby, one can achieve a heating pad where the majority of the pad is cycling at a lower temperature than if the thermostat sensed the main area of the heating pad.

In order to achieve an intermediate temperature for the pad, the intermediate contact can be wired with a diode in series, which will cut the power to that portion by fifty percent (50%), thereby the temperature at that point would not rise as rapidly as it did when the diode was out of the circuit and an intermediate pad temperature could be achieved.

The way to control the circuit is simply achieved by the use of a multiple position switch which is located in a control box external to the heating pad, which is actually attached to the line cord so that it could stay remote from the heating pad which needs to stay flexible and soft.

DETAILED DESCRIPTION OF THE DRAWINGS

In the drawings wherein like reference characters denote similar elements throughout the several views:

FIG. 2-A is a cross section along lines 2A—2A of FIG. 1;

FIG. 2-B is a cross section along lines 2B—2B of FIG. 1;

FIG. 8-A illustrates the electrically conductive sheet of FIG. 6 operating at a "high" heat setting, along with current flow lines added to clarify the operation of the pad;

FIG. 8-B illustrates the electrically conductive sheet of FIG. 6 operating at a "low" heat setting, along with current flow lines added to clarify the operation of the pad;

DETAILED DESCRIPTION OF THE PRESENTLY PREFERRED EMBODIMENTS

Figure 1:
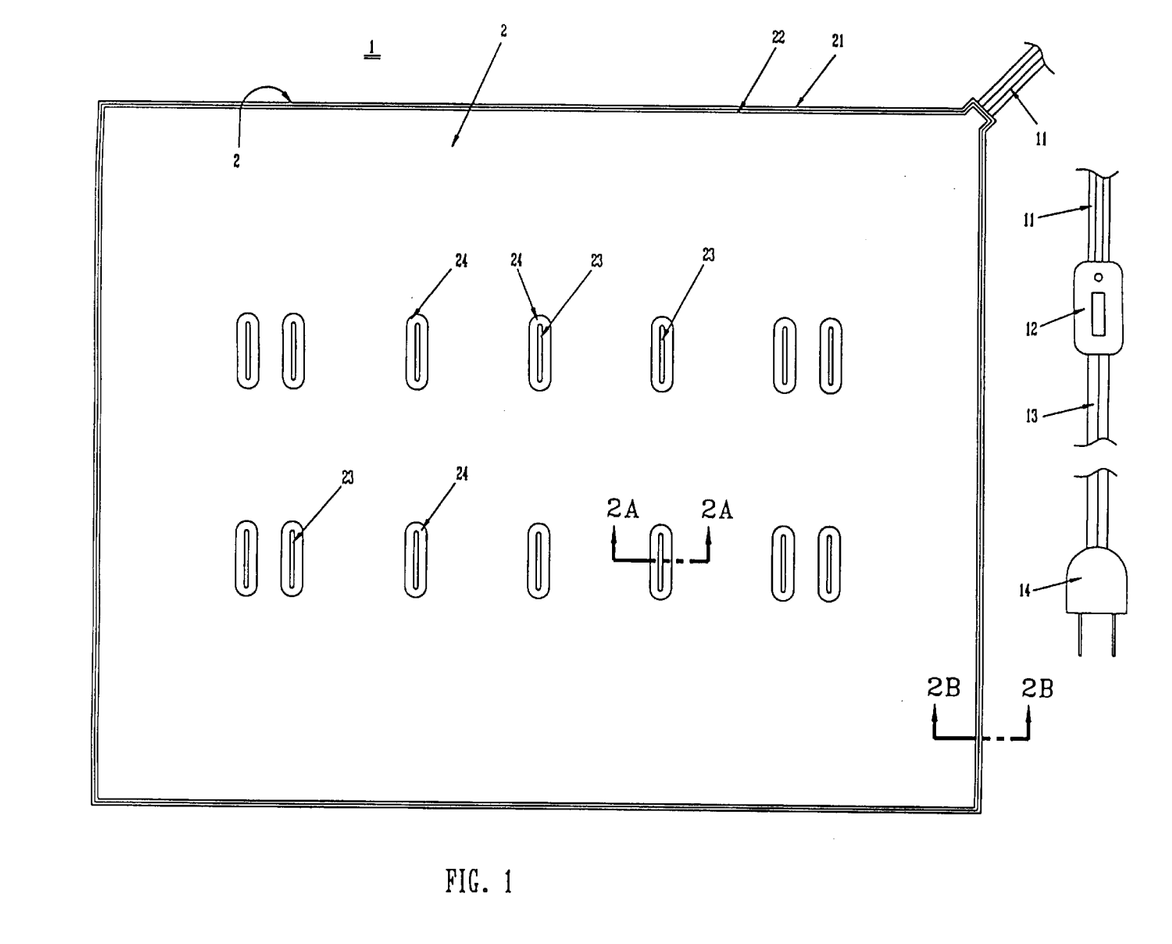
FIG. 1 is an overhead plan view of the heating pad according the invention.

Referring now to the drawings for a more detailed description of the present invention and more particularly to FIG. 1 thereof, where the heating pad is denoted generally as element 1 and is shown in plan view and where a three lead cord 11 is shown in a disconnected form which leads it to the control box 12 from where a two lead cord 13 is connected to the plug 14 that intends to be plugged into the electrical outlet. Typically, the distance from the end of the heating pad to the switch is in the range of 15 to 20 inches whereas the distance from the switch to the electrical outlet is in the range of 6 feet allowing the user to be fairly removed from the wall outlet in case the user needs to use the heating pad while lying in bed. The heating pad I shows an outer perimeter 21 represented by triple lines. These triple lines represent a seam 22 whereby the two outer vinyl sheets 2 and 2' are adhered onto themselves to create a waterproof seal. The two outer vinyl sheets 2, 2' are also sealed to the three lead cord 11 which is covered with vinyl similar to the vinyl used for the outer sheet and which is therefore capable of being adhered to the outer envelope. The sealing is achieved by a die that is heated by means of radio frequency or other means which causes the vinyl sheets to melt and to fuse to each other. In a similar way, a plurality of internal seams or stitches 23 are illustrated, each internal seam or stitch 23 having an oval depression 24. These stitches 23 hold the two outer layers or sheets of vinyl 2, 2' together and also trap between them the electrically conductive sheet 3 and the foam covers 4 and 4' surrounding the conductive sheet 3 as will be further described.

Figure 2A:
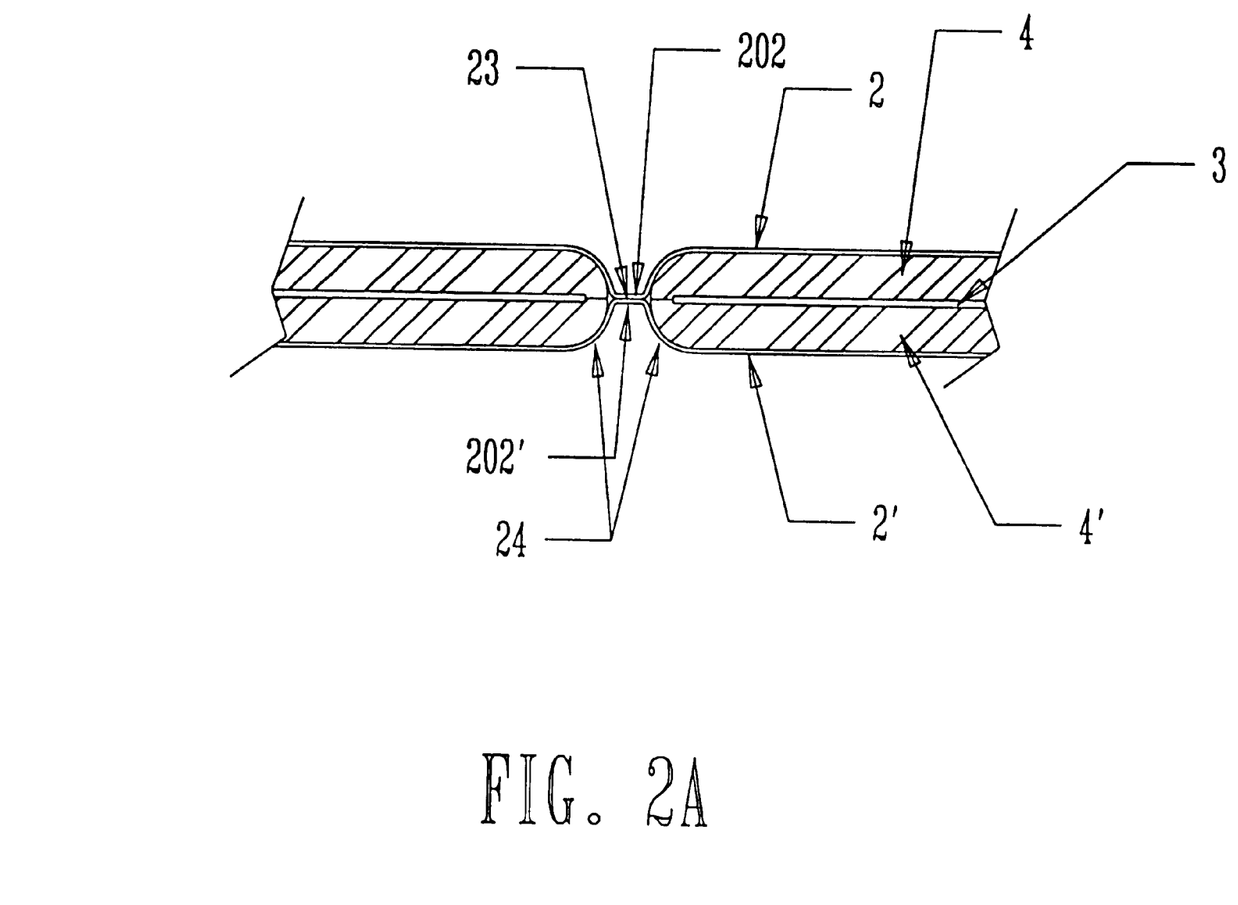

Referring now to FIG. 2A, where the internal seam or stitch 23 that holds the outer layers of vinyl 2, 2' is showed in greater detail and enlargement. The two outer layers of vinyl 2, 2' each have seal areas 202, 202' that are brought together and fused to each other in an area which is clear of both the electrically conductive sheet 3 and the surrounding foam material 4, 4'. The seal areas 202, 202' which create the seam 23, prevent the movement of the electrically conductive sheet 3 and also help locate the foam layers 4, 4' that surround the conductive sheet 3.

Figure 2B:
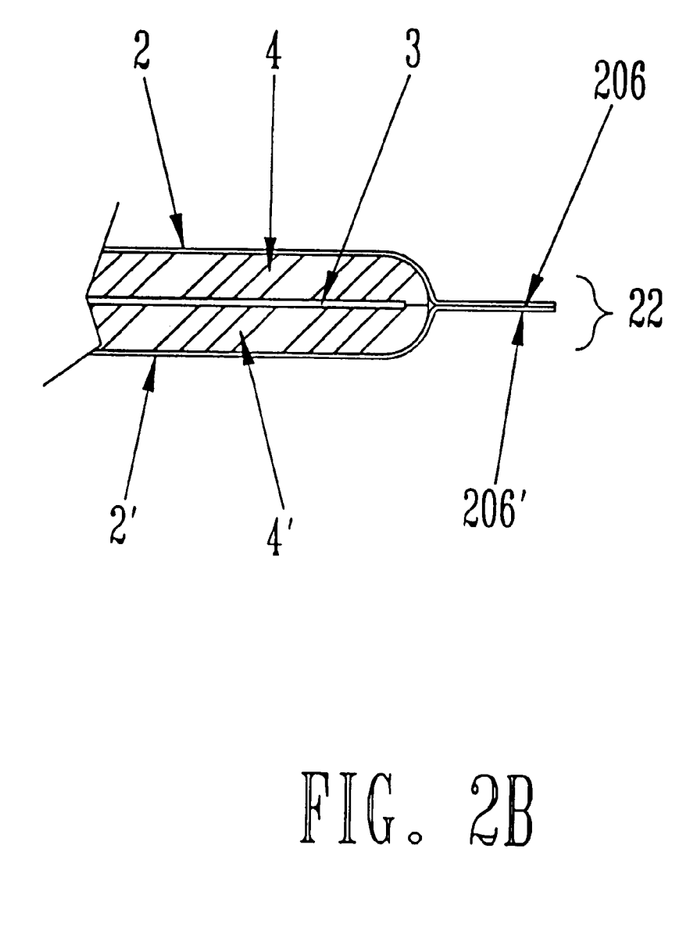
Figure 3:
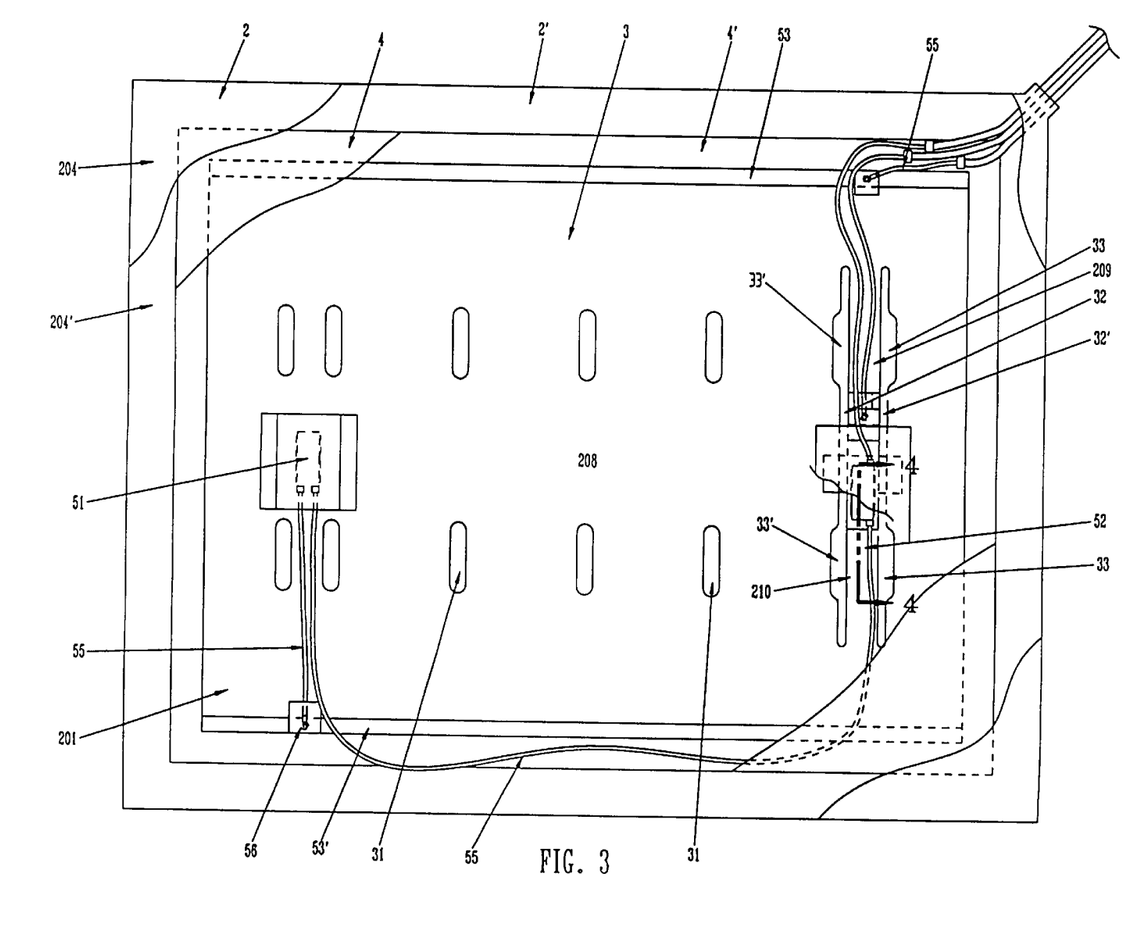
FIG. 3 is an overhead plan view of the heating pad shown in FIG. 1 except that the outer vinyl layer is partially removed as is the inner foam pad, revealing the electrically conductive sheet, the wire leads, and the controlling thermostats.

With reference to FIG. 2B, outer perimeter seam 22 is shown in cross section. The first and second sheet materials 2, 2' are brought together and fused to each other along respective sealing edges 206, 206'. As shown in FIG. 3, sealing edges 206, 206' are defined as the perimeters of the sheet material 2, 2' that extend over the conductive sheet 3. Referring to both FIGS. 2A and 2B, when the sealing edges 206, 206' of the first and second sheets 2, 2' are aligned together, the sealing area 202 and the sealing edge 206 of the first sheet 2 are fused together with the sealing area 202' and the sealing edge 206' of the second sheet 2' so that the conductive sheet 3 is sealed within the first and second sheet material 2, 2' to define the seam 22. As is also shown in FIG. 2B, the seam 22 encloses foam layers 4, 4'.

FIG. 3, which shows the conductive sheet 3 of FIG. 1 with the exterior vinyl sheet 2 as well as the upper foam layer 4 partially removed, illustrates the electrical connections and the placements of the two thermostats 51 and 52. As shown, thermostat 51 is located in the main heating body 208 of the conductive sheet 3, and thermostat 52 is located on an elongate heating zone 209 that is separated from the main heating body 208 by two elongated strips 32 and 32'. FIG. 3 also illustrates the elongated openings 31 in the electrically conductive sheet 3 through which the outer vinyl sheets 2, 2' are fused, or seamed onto themselves. Additionally, FIG. 3 illustrates the electric wires and the connections to the thermostats and to the elongated conductive strips 53 and 53' that are attached to the two ends of the electrically conductive sheet 3.

As shown in FIG. 3, the first sheet material 2 is provided with a perimeter 204, the perimeter 204 being larger than the perimeter 201 of conductive sheet 3 so as to extend over the conductive sheet 3 and thus define the sealing edge 206, as described previously. As well, second sheet material 2' is also provided with a perimeter 204', the perimeter 204' also being larger than the perimeter 201 of the conductive sheet 3 so as to extend over the conductive sheet 3. In a similar manner to the first sheet material 2, the second sheet material 2' is provided with a sealing edge 206' such that when the conductive sheet 3 is placed between the first and second sheet materials 2, 2', and when the sealing edges 204, 204' of the first and second sheet material 2, 2' are aligned together, the sealing area 202 and the sealing edge 204 of the first sheet 2 are ed together with the sealing area 202' and sealing edge 204' of the second sheet 2' so that the conductive sheet 3 is sealed within the first and second sheet material 2, 2' to define a watertight pouch.

Figure 4:
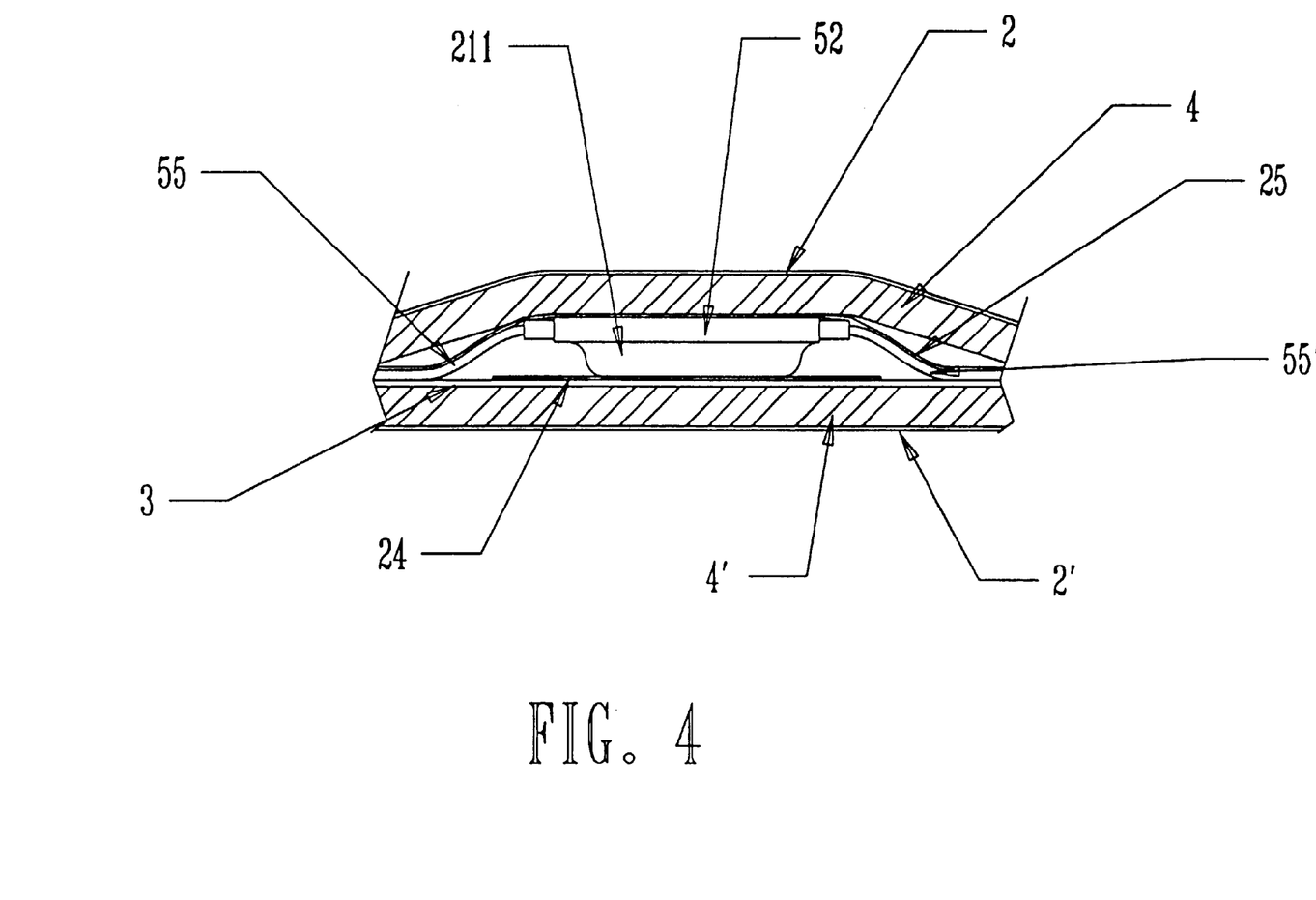
FIG. 4 is a cross section along lines 4—4 of FIG. 3 showing the position of the thermostat controlling the temperature of the pad.

FIG. 4 which is a cross section through the heating pad 1, illustrates the manner in which the thermostats 51 and 52 are held in place and are electrically insulated from the electrically conductive sheet 3. Tape 24 is provided with adhesive on both sides, so it sticks to the electrically conductive sheet 3 as well as to a thermostat case 211 which contains thermostat 52, insuring good and consistent as well as repeatable heat transfer from the thermostat 52. Tape strip 25 insures additional securing for the thermostat 52 as well as provides protection against the sharp edges of the thermostat case 211 from digging into foam layer 4. Electric leads 55 are shown connected to the thermostat case 211 which contains the thermostat switching components 52.

Figure 5:
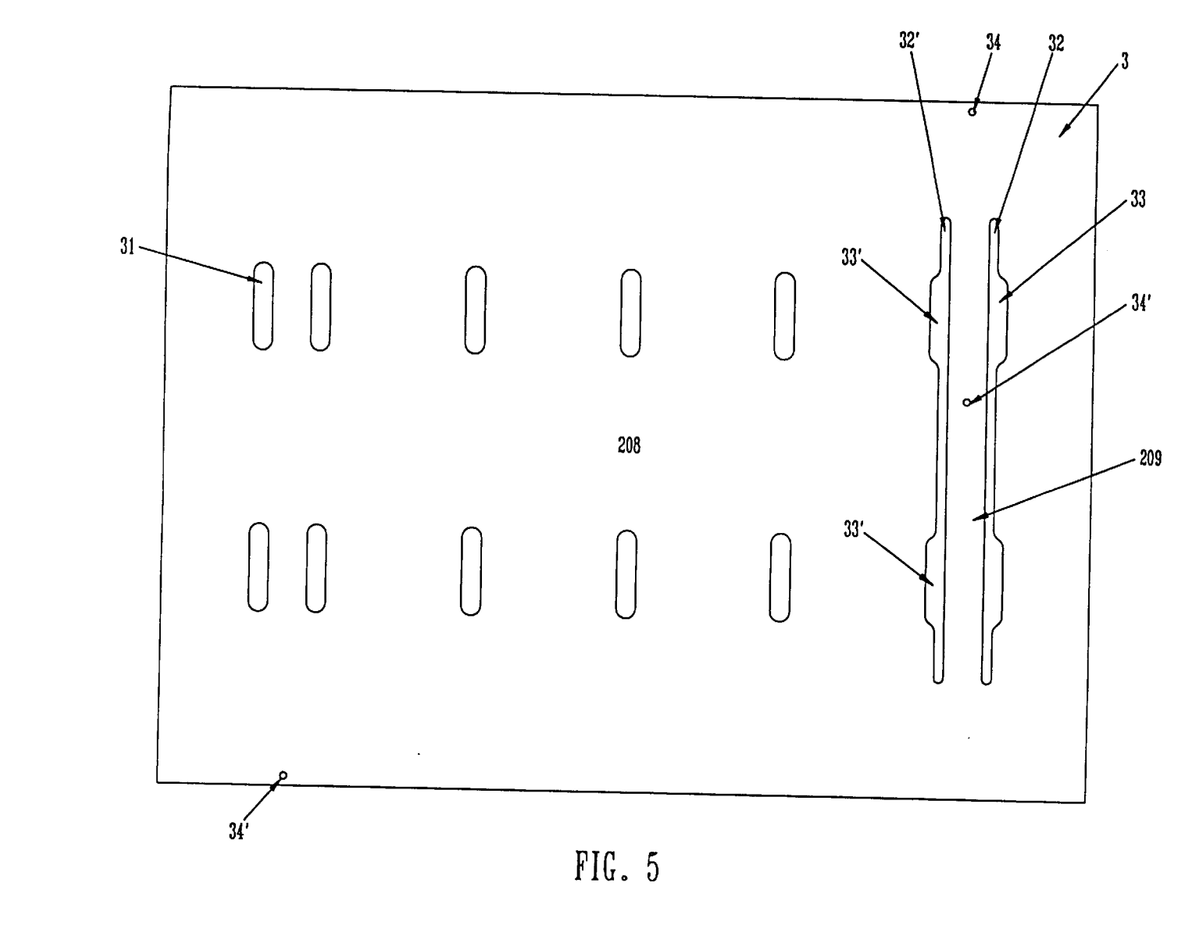
FIG. 5 shows the electrically conductive sheet of FIGS. 1 and 3.

FIG. 5 illustrates the electrically conductive sheet 3 in its initial state where it was cut to size and perforated with elongated openings 31 as well as by two elongated cuts 32 and 32' which created the elongate heating zone 209 which would be used, as will be further discussed, to create different temperature settings at which the heating pad 1 can be operated. Portions 33, 33' of the elongated cuts, similar in length to the openings 31, are widened so as to serve as openings through which the vinyl sheets could be seamed, to help anchor the narrow portion of the electrically conductive sheet 3 defined by the two cuts 32 and 32'.

Figure 6:
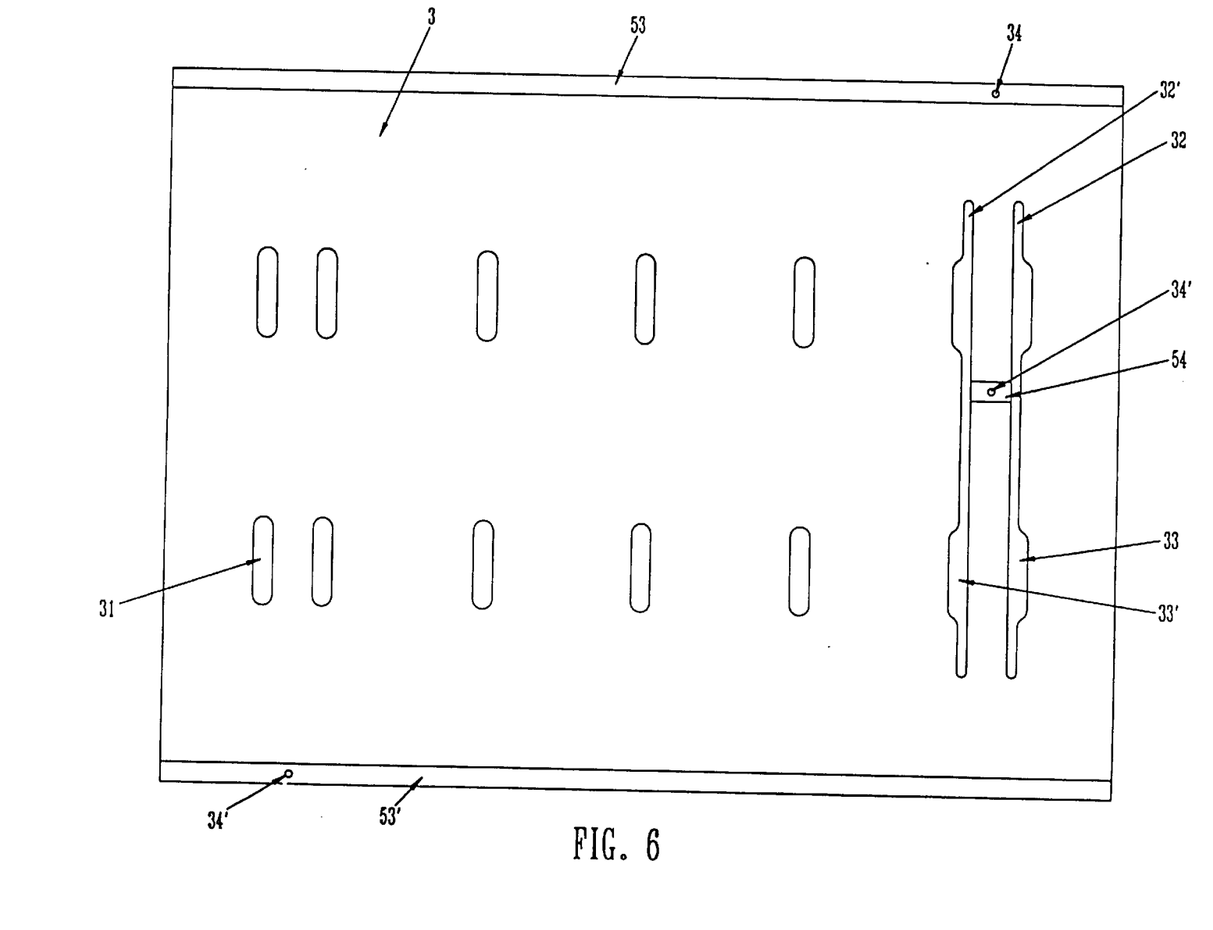
FIG. 6 illustrates the electrically conductive sheet of FIG. 5 wherein the conductive tape strips on opposite ends of the heater are shown as well as the shortening strip is shown.

In FIG. 6, the electrically conductive sheet of FIG. 5 is shown with the addition of the two conductive strips 53 and 53' along the longer sides of the electrically conductive sheet 3 as well as the conductive pad 54 located within the elongated heating zone 209 of the electrically conductive sheet 3, defined by the elongated strips 32 and 32'. Perforations 34 are used for securing electric leads 55 to the conductive strips 53, 53' by eyelets 56 or similar connectors, the eyelets 56 being shown in FIGS. 3 and 8B.

Figure 7:
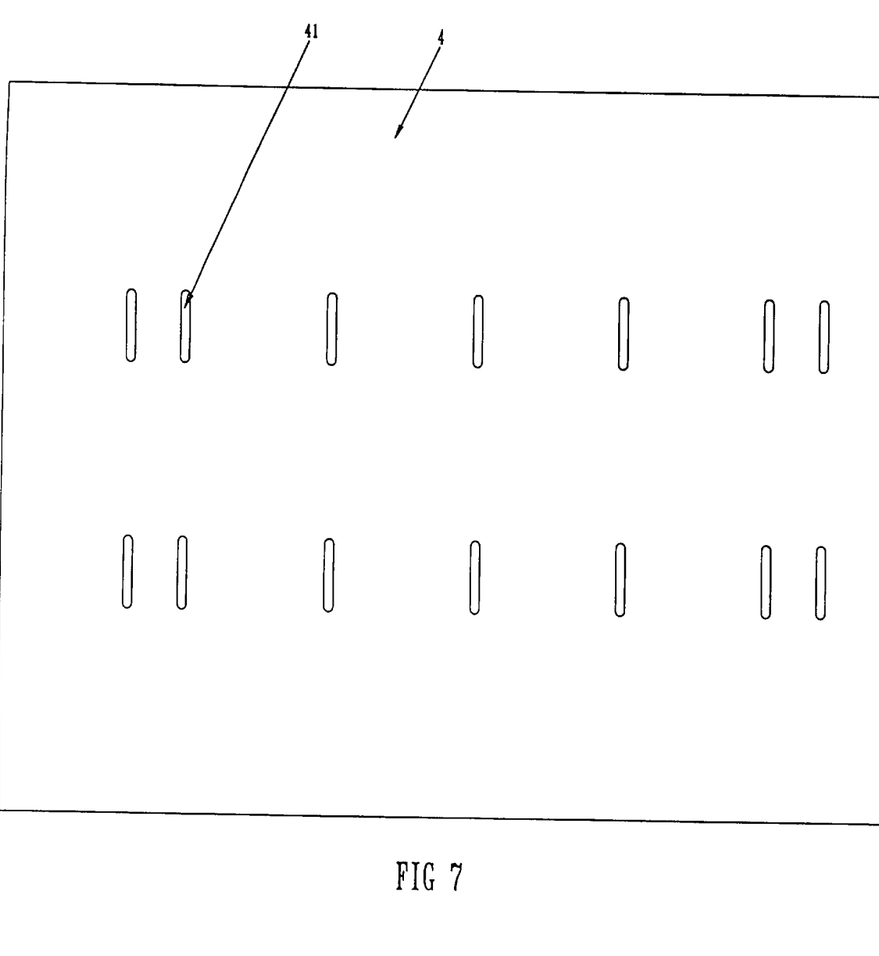
FIG. 7 is an overhead plan view of the foam pad that covers both sides of the electrically conductive sheet in FIG. 3.

FIG. 7 illustrates the foam sheet 4, 4' that is placed around the electrically conductive sheet 3 to provide for electrical insulation as well as temperature fluctuation attenuation. The foam sheet 4 is characterized by a number of oval slots 41 which correspond in their location to slots 31 in the electrically conductive sheet 3 but are smaller in size than the slots 31.

Figure 8A:
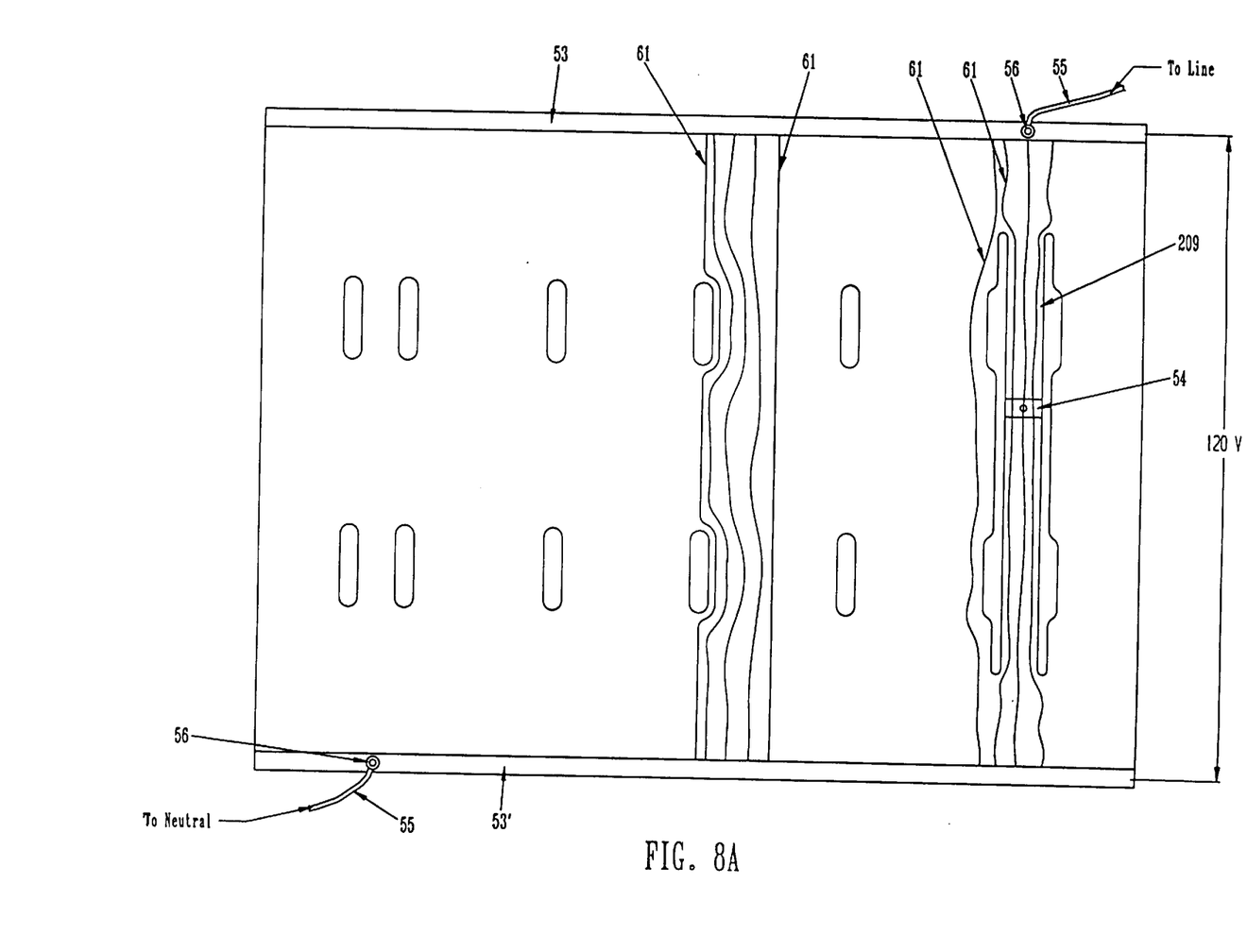
Figure 8B:
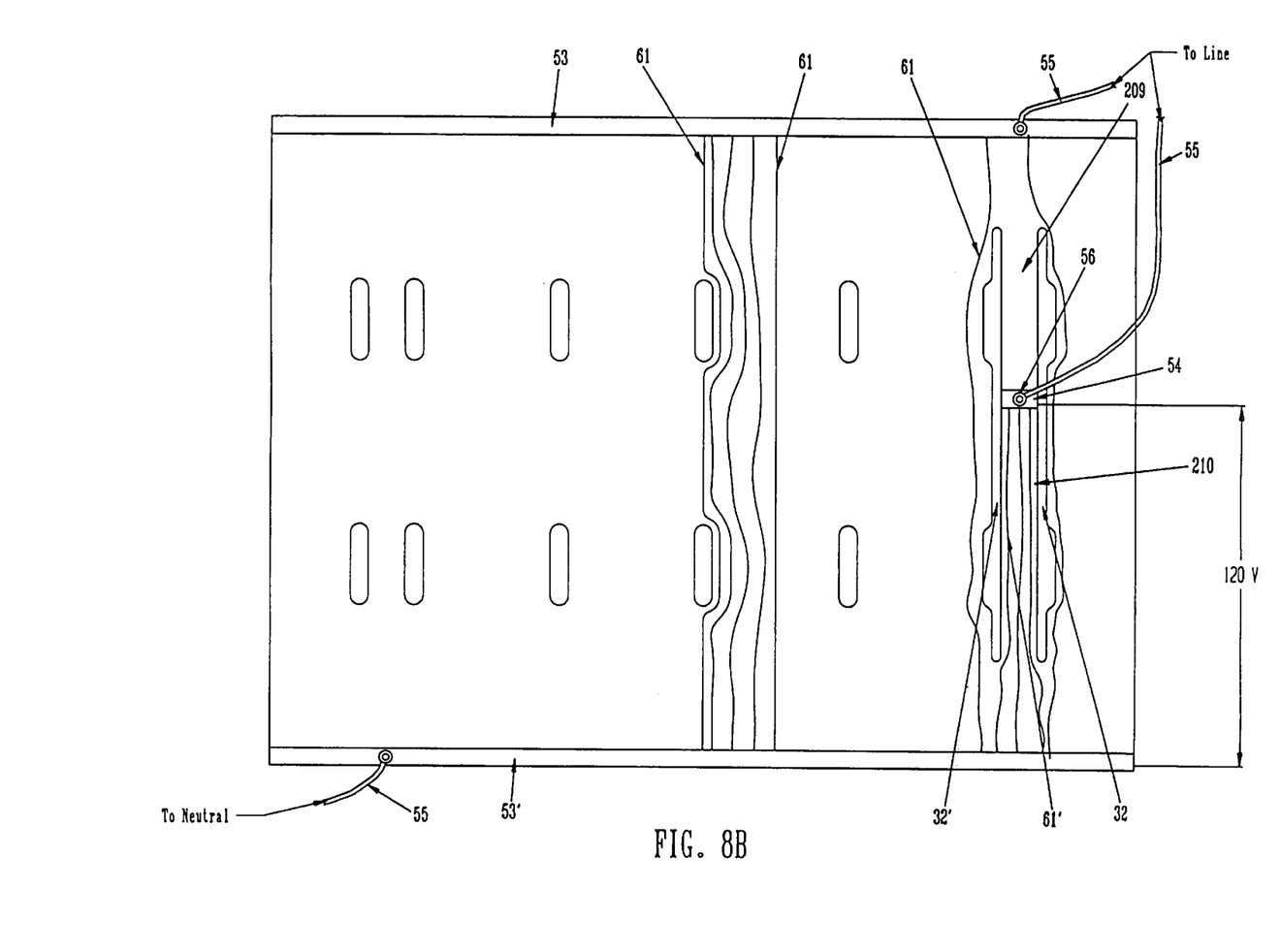

FIGS. 8-A and 8-B are similar to FIG. 6 except that they show the current flow lines 61 as contemplated by the invention. One will note that in FIG. 8-A the two conductive strips 53, 53' are connected to the line and to neutral thereby the voltage between 53 and 53' would be line voltage, namely 120 volts and the current would flow between these two in a fashion as illustrated in FIG. 8-A. In FIG. 8-B, however, the pad 54 is shown as being connected to the lead that emanates from conductive strip 53 and therefore, there will be no difference in potential (voltage difference) between pad 54 and conductive strip 53. This would result in a voltage drop in line voltage between pad 54 and conductive strip 53, which would be responsible for a high current flow line 61', and consequently would generate a higher temperature in the heated portion 210 of elongate heating zone 209, which is the region defined between pad 54 and strip 53' and also confined by the elongated cuts 32 and 32'.

Referring back now to FIG. 3, it should be noted that thermostat 52 is located in the area previously defined as the heated portion 210 of elongate heating zone 209 which is the high current flow, high temperature area. In the event that pad 54 and strip 53 are connected, thermostat 52 would be exposed to higher temperatures than thermostat 51 and it will therefore shut down the entire power to the pad sooner than thermostat 51 would have. This is the method being used, as previously discussed, for maintaining a lower overall temperature on the pad.

Figure 9:
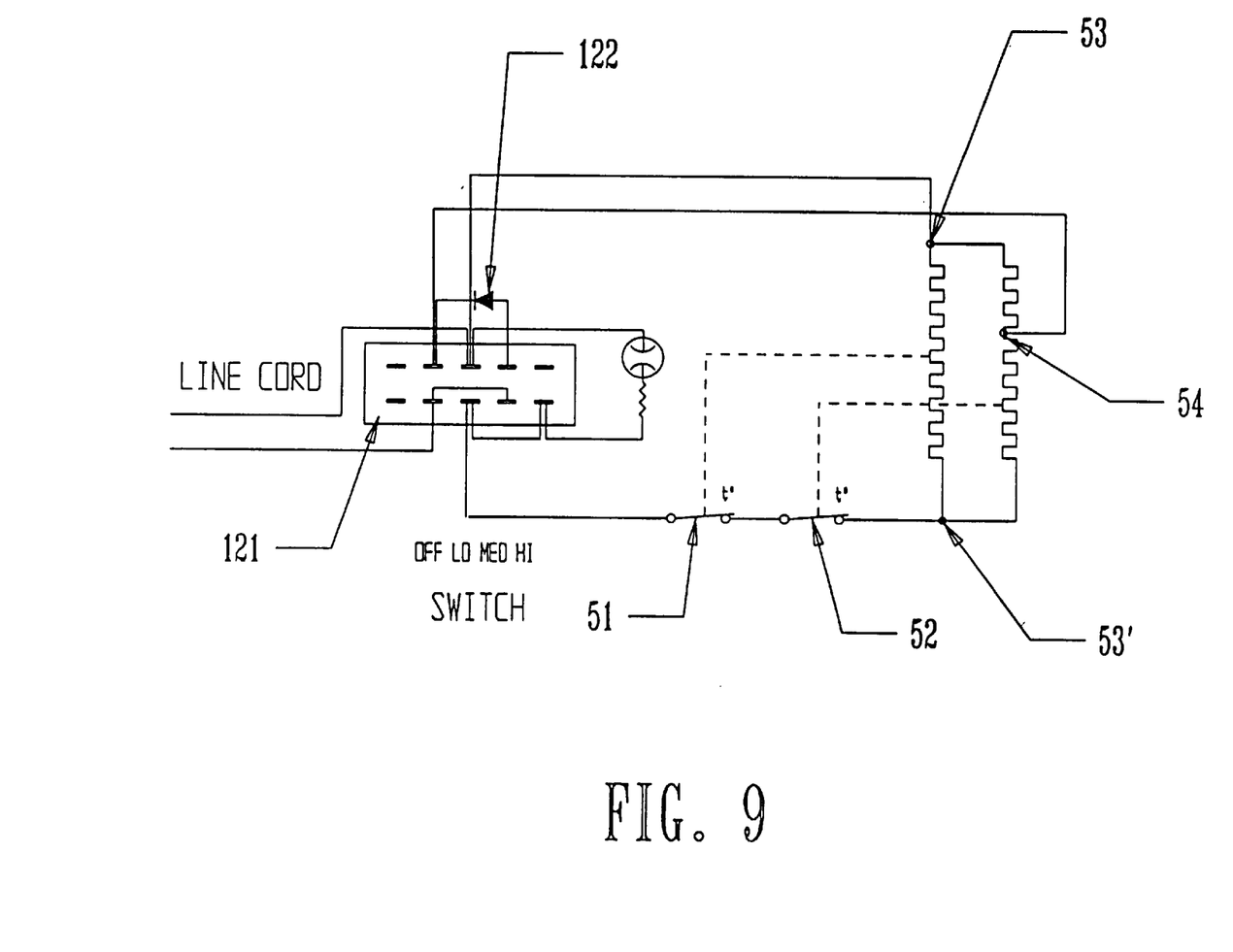
FIG. 9 is an electric diagram showing how the two thermostats are being controlled in order to provide multiple heat settings.

Referring now to FIG. 9, one can see that when the switch 121 is positioned in the low setting, that the power would be supplied to strips 53 and 53', but that 53 would also be connected to pad 54 thereby, as previously explained, causing increased flow between 54 and 53' resulting in higher heat generated and the early opening of thermostat 52. On the other hand, when the switch 121 is set to the medium setting, you will note that diode 122 is wired in series with pad 54 thereby reducing by half, the amount of current flowing between 54 and 53 and causing the thermostat 52 to open later than if the current would have been unimpeded by the introduction of the diode 122, thereby getting a temperature setting that is halfway between the low setting and the high setting of the switch.

Figure 10:
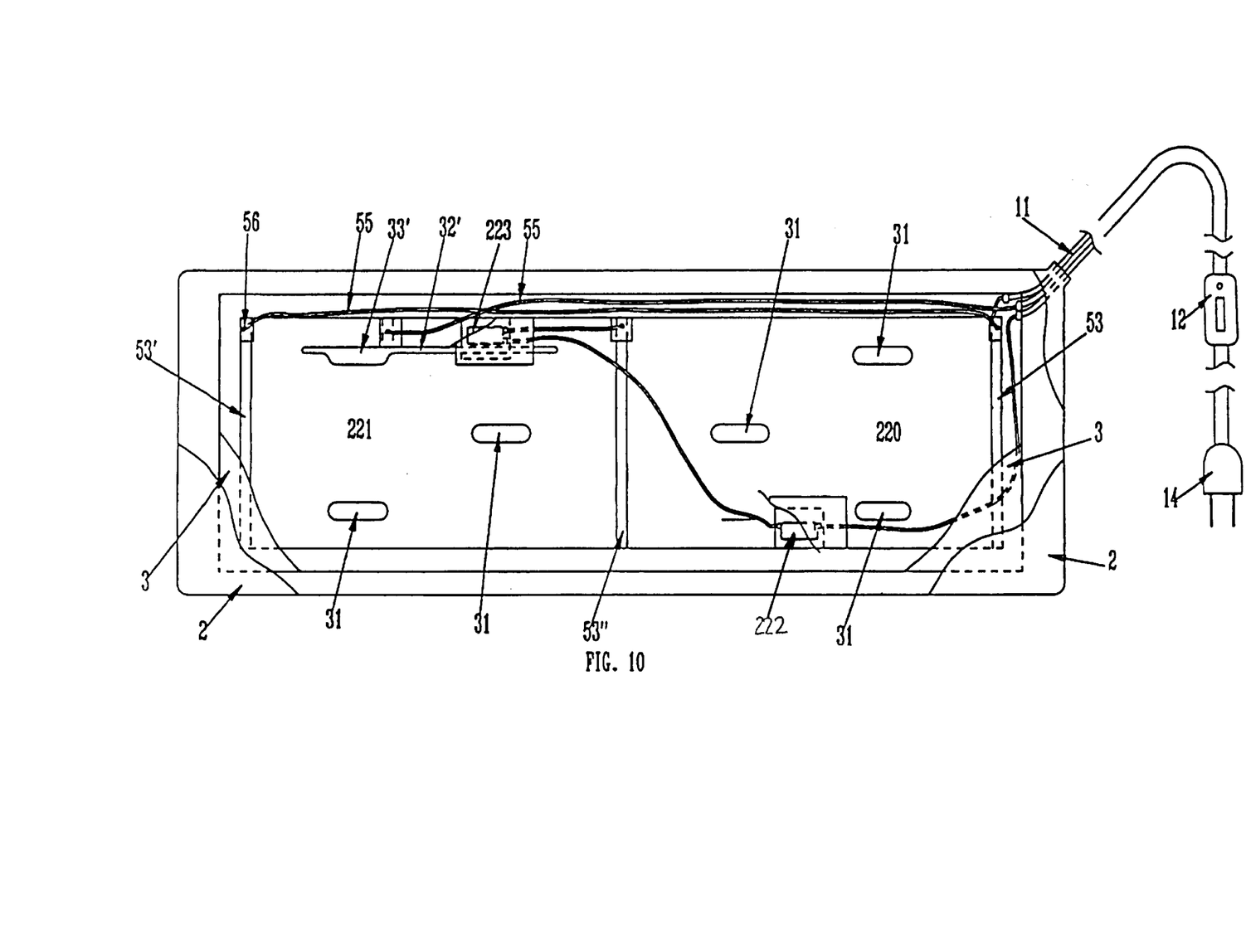
FIG. 10 is an overhead plan view of a further embodiment of the heating pad.

With reference to FIG. 10, a further embodiment of the heating pad 1 is shown and described. Similar to the embodiment shown in FIG. 3, the heating pad 1 is provided with a conductive sheet 3 having elongated openings 31 and a perimeter. First and second sheet material 2, 2' which are provided with seal areas and sealing edges are disposed about first and second foam sheets 4, 4' that surround the conductive sheet 3 so that the first and second foam sheets 4, 4' as well as the conductive sheet 3 is sealed within the first and second sheet material 2, 2' to define a water-tight pouch. Similar to the embodiment described in FIG. 3, the seal areas of the first and second sheet material 2, 2' retain the conductive sheet 3 from movement relative to the first and second sheet materials 2, 2'. However, heating pad 1 is provided with an intermediate conductive strip 53" which is positioned between the first and second conductive strips 53, 53' in such a way so as to define first and second heating bodies 220, 221. The first and intermediate conductive strips 53, 53" are connected to a source of electric current and define a first circuit. As well, the second and intermediate conductive strips 53', 53" are also connected to a source of electric current and define a second circuit. The first and second heating bodies 220, 221 are provided with first and second thermostats 222, 223 so that both first and second circuits are wired in parallel. When a predetermined temperature in the second heating body 221 is sensed by the second thermostat 223, electric current is shut off to both first and second heating bodies 220, 221.

It should be understood that the preferred embodiments and examples described herein are for illustrative purposes only and are not to be construed as limiting the scope of the present invention which is properly delineated only in the appended claims.

It should also be understood that the drawings are not necessarily drawn to scale, but that they are merely conceptual in nature.

What is claimed is:

1. An electric heating pad, comprising:

a conductive sheet adapted to receive an electric current flow, said conductive sheet having a perimeter;

a first sheet material, having a closure area disposed on said first sheet material and a perimeter larger than the perimeter of said conductive sheet so as to extend over said conductive sheet to define a closing edge; and a second sheet material, having a closure area disposed on said second sheet material and a perimeter larger than the perimeter of said conductive sheet so as to extend over said conductive sheet to define a closing edge, so that when said conductive sheet is placed between said first and second sheet material and when the closing edges of said first and second sheet material are aligned together, the closing area and the closing edges of said first sheet are affixed together with the closing area and the closing edges of said second sheet so that said conductive sheet is sealed within said first and second sheet material to define a pouch.

2. The electric heating pad of claim 1, further comprising more than one conductive strips attached to said conductive sheet, said conductive strips connected to a source of electric current so that when said electric current flows through said conductive sheet heat will be generated in a main heating body.

3. The electric heating pad of claim 1, wherein said conductive sheet further comprises a plurality of openings and wherein said first and second sheet material further comprises a plurality of closure areas.

4. The electric heating pad of claim 3, further comprising a third sheet material sandwiched between said first sheet material and said conductive sheet, said third sheet material provided with a plurality of slots which correspond to said plurality of openings of said conductive sheet, said slots allowing said plurality of closure areas of said first and second sheet material to abut in direct contact.

5. The electric heating pad of claim 4, further comprising a forth sheet material sandwiched between said second sheet material and said conductive sheet, said forth sheet material provided with a plurality of slots which correspond to said plurality of openings of said conductive sheet, said slots allowing said plurality of closure areas of said first and second sheet material to abut in direct contact.

6. The electric heating pad of claim 1, further comprising a circuit means for varying the electrical current flow through said conductive sheet.

7. The electric heating pad of claim 2, wherein said conductive sheet is provided with more than one substantially parallel elongated cuts, said elongated cuts being substantially perpendicular to said conductive strips so that elongated cuts define an elongate heating zone therebetween.

8. The electric heating pad of claim 7, wherein said conductive sheet is provided with a secondary electrical contact positioned between said elongated cuts and between said conductive strips such that when said secondary electric current is connected to a source of electric current, electric current flows from said secondary electrical contact to one of said conductive strips through a heated portion of said elongate heating zone.

9. The heating pad of claim 8, further comprising a first thermostat mounted within said heated portion of said elongate heating zone for sensing a predetermined temperature therein such that when said predetermined temperature is reached, electric current is shut off to said main heating body.

10. The electric heating pad of claim 9, further comprising a second thermostat mounted in said main heating body.

* * * * *